United States Patent
Kathe et al.

(10) Patent No.: US 8,932,873 B2
(45) Date of Patent: Jan. 13, 2015

(54) METHOD FOR MONITORING CONCENTRATION OF WATER BORNE SUBSTANCE IN AN AQUEOUS MEDIUM

(75) Inventors: Ulrich Kathe, Leonberg (DE); Thomas Schipolowski, Stuttgart (DE); Oliver Bettmann, Rüsselsheim (DE); Björn Emling, Reinheim (DE)

(73) Assignee: Endress + Hauser Conducta Gesellschaft fur Mess- und Regeltechnik mBH + Co. KG, Gerlingen (DE)

( * ) Notice: Subject to any disclaimer, the term of this patent is extended or adjusted under 35 U.S.C. 154(b) by 624 days.

(21) Appl. No.: 12/448,093

(22) PCT Filed: Nov. 30, 2007

(86) PCT No.: PCT/EP2007/063063
§ 371 (c)(1),
(2), (4) Date: Feb. 23, 2010

(87) PCT Pub. No.: WO2008/068196
PCT Pub. Date: Jun. 12, 2008

(65) Prior Publication Data
US 2010/0178706 A1 Jul. 15, 2010

(30) Foreign Application Priority Data
Dec. 7, 2006 (DE) .......................... 10 2006 058 051

(51) Int. Cl.
*G01N 33/00* (2006.01)
*G01N 33/18* (2006.01)

(52) U.S. Cl.
CPC .................................. *G01N 33/1846* (2013.01)
USPC ........... 436/146; 436/114; 436/116; 436/145; 422/82.05

(58) Field of Classification Search
None
See application file for complete search history.

(56) References Cited

U.S. PATENT DOCUMENTS

| 5,340,542 A | 8/1994 | Fabinski |
| 5,981,289 A | 11/1999 | Wright |

(Continued)

FOREIGN PATENT DOCUMENTS

| DE | 197 27 839 | 1/1999 |
| DE | 199 20 580 C1 | 12/2000 |

(Continued)

*Primary Examiner* — Robert Xu
(74) *Attorney, Agent, or Firm* — Bacon & Thomas, PLLC

(57) ABSTRACT

A method for monitoring the concentration of water borne substances in an aqueous medium, by introducing a defined amount of the aqueous medium into a gas circulatory system of an analytical apparatus which extends through a high temperature reaction chamber and a measuring chamber. The introducing of the aqueous medium occurs upstream of the high temperature reaction chamber or into it. The aqueous medium is evaporated in the high temperature reaction chamber, the water borne substance with at least one reaction partner in the high temperature reaction chamber reacts to a gaseous reaction product, and a current value of a measured variable is registered, which is a function of the concentration of the chemical species of the reaction product in the gas circulatory system. The concentration of the chemical species of the reaction product in the gas circulatory system depends, on the one hand, on a time-dependent state of the gas circulatory system and, on the other hand, on the concentration of the substance in the aqueous medium; ascertaining the concentration of the substance in the aqueous medium by applying the current value of the measured variable, wherein, in the ascertaining of the concentration of the substance in the aqueous medium, the contribution to the concentration of the chemical species of the reaction product in the gas circulatory system by the state of the gas circulatory system is ascertained on the basis of a model of the state, and a correction of the concentration of the chemical species of the reaction product in the gas circulatory system occurs on the basis of this contribution.

18 Claims, 1 Drawing Sheet

(56) References Cited

U.S. PATENT DOCUMENTS

| | | |
|---|---|---|
| 6,143,568 A | 11/2000 | Pilz |
| 2006/0062691 A1* | 3/2006 | Bauman et al. ............. 422/62 |
| 2008/0026482 A1 | 1/2008 | Arts |

FOREIGN PATENT DOCUMENTS

| | | |
|---|---|---|
| DE | 199 31 801 A1 | 1/2001 |
| DE | 20 2004 000 483 U1 | 5/2004 |
| DE | 103 60 445 A1 | 7/2005 |
| GB | 2295232 A | 5/1996 |
| JP | 61088150 A | 5/1986 |
| JP | 6421357 | 2/1989 |
| JP | 6421358 | 2/1989 |
| JP | 3115859 | 5/1991 |

* cited by examiner

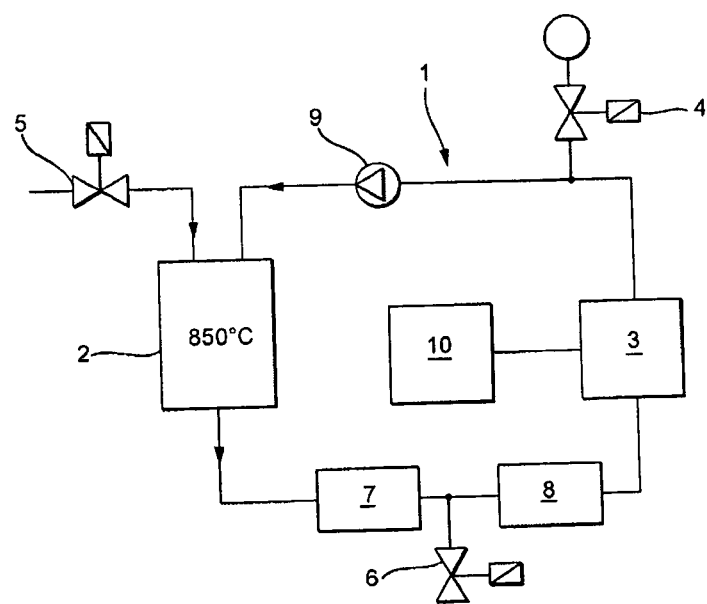

US 8,932,873 B2

METHOD FOR MONITORING CONCENTRATION OF WATER BORNE SUBSTANCE IN AN AQUEOUS MEDIUM

TECHNICAL FIELD

The present invention relates to a method for monitoring concentration of water borne substance in an aqueous medium.

BACKGROUND DISCUSSION

An example of a water borne substance is total organic carbon, TOC, which is measured after oxidation to carbon dioxide via ascertainment of the carbon dioxide concentration. Another example of a water borne substance is total bound nitrogen, TNb.

Monitoring methods for water borne substances are discussed, for example, in DE 199 20 580 C1 and DE 197 27 839 A1. Furthermore, analytical devices for performing the described monitoring methods are available, for example, from Endress+Hauser under the mark "STIP-toc".

Methods of the field of the invention comprise essentially the following steps:
introducing a defined amount of aqueous medium into a gas circulatory system of an analytical apparatus comprising a high temperature reaction chamber and a measuring chamber, wherein the gas circulatory system extends through the high temperature reaction chamber and the measuring chamber, and wherein the introducing of the aqueous medium occurs upstream from the high temperature reaction chamber;
evaporating the aqueous medium in the high temperature reaction chamber;
burning the water borne substance in the high temperature reaction chamber to a reaction product;
registering current value of a measured variable, which is a function of concentration of the chemical species of the reaction product in the gas circulatory system, wherein the concentration of the chemical species of the reaction product in the gas circulatory system depends, on the one hand, on a time-dependent state of the gas circulatory system and, on the other hand, on the concentration of the substance in the aqueous medium; and
ascertaining the concentration of the substance in the aqueous medium by applying the current value of the measured variable.

The ascertaining of the concentration of the reaction product occurs, usually, photometrically. For ascertaining TOC, the carbon is, usually, oxidized, thus burned, and the resulting carbon dioxide concentration in the gas circulatory system is ascertained photometrically with an infrared absorption measurement. The measuring can, on the one hand, be performed in a batch method, wherein a sample amount is burned and leads correspondingly to a short signal peak, which must be integrated, when the product of combustion is not circulated in a circulatory system. In a circulatory method, the product of combustion is homogeneously distributed and leads to a uniform signal. Injection of the aqueous medium in a continuous method leads, due to the described distribution of the product of combustion in the gas circulatory system, to a smoothing, or inertia in the data. Additionally, the continuous method has the problem that contamination of the gas circulatory system, which corrupts the measurements, cannot be recognized, unless control measurements occur, which then interrupts the continuous method.

In the batch method, there is, indeed, the opportunity, between individual batches, to clean the gas circulatory system and to perform control measurements; however, in such case, too much measurement time can be used for these control measurements.

SUMMARY OF THE INVENTION

It is, consequently, an object of the invention to provide a method, which satisfies the need for accuracy of measurement at a lessened number of reference measurements.

The method of the invention for monitoring concentration of water borne substance in an aqueous medium includes steps as follows:
introducing a defined amount of the aqueous medium into a gas circulatory system of an analytical apparatus comprising a high temperature reaction chamber and a measuring chamber, wherein the gas circulatory system extends through the high temperature reaction chamber and the measuring chamber, and wherein the introducing of the aqueous medium occurs upstream from the high temperature reaction chamber or into it;
evaporating the aqueous medium in the high temperature reaction chamber;
burning the water borne substance in the high temperature reaction chamber to a reaction product;
registering current value of a measured variable, which is a function of concentration of the chemical species of the reaction product in the gas circulatory system, wherein the concentration of the chemical species of the reaction product in the gas circulatory system depends, on the one hand, on a time-dependent state of the gas circulatory system and, on the other hand, on the concentration of the substance in the aqueous medium; and
ascertaining the concentration of the substance in the aqueous medium by applying the current value of the measured variable;
wherein, additionally,
in the ascertaining of the concentration of the substance in the aqueous medium, the contribution to the concentration of the chemical species of the reaction product in the gas circulatory system by the state of the gas circulatory system is ascertained on the basis of a model of the state, and a correction of the concentration of the chemical species of the reaction product in the gas circulatory system occurs on the basis of this contribution.

The reaction partner can, for example, be present as carrier gas in the gas circulatory system. A carrier gas can be, for example, $CO_2$-free air or $O_2$. Furthermore, catalysts can serve in the high temperature reaction chamber as reaction partner.

In an embodiment of the invention for producing a clean state of the gas circulatory system, the gas circulatory system, at given times or state dependently, is purged with carrier gas free of the chemical species of the reaction product, except for possible negligible impurities.

In a presently preferred, further development of this embodiment of the invention, a current value of the measured variable is registered, directly after the purging with the carrier gas and before new introducing of the aqueous medium, as reference value, especially as null point for describing clean state of the gas circulatory system, for ascertaining the concentration of the chemical species of the reaction product in the gas circulatory system.

In a case where the chemical species of the reaction product can get from the environment of the analytical apparatus as contaminant into the gas circulatory system, the model, in an additional embodiment of the invention, describes time-dependent changing of the concentration of the chemical species of the reaction product in the gas circulatory system due to contamination.

Following the purging with the carrier gas, in a further development of the invention, time behavior of the measured variable without introducing additional sample of the aqueous medium is observed, in order to win current data for modeling of the time behavior of the concentration on the basis of contamination.

The modeling of the time behavior of the concentration on the basis of contamination can, for example, comprise a diffusion model.

In an embodiment of the invention, the gas circulatory system is not purged with the carrier gas after each ascertaining of the concentration of the chemical species of the reaction product. Instead, there occurs after a first introducing of a first defined amount of aqueous medium into the gas circulatory system and the following ascertaining of the concentration of the chemical species of the reaction product, at least one further introducing of a second defined amount of an aqueous medium into the gas circulatory system, wherein, subsequently, the then present concentration of the chemical species of the reaction product is ascertained on the basis of the current value of the measured variable, and the current concentration of the substance in the second defined amount of the aqueous medium is ascertained on the basis of the concentration of the chemical species of the reaction product in the gas circulatory system and the model of the state of the gas circulatory system. Entered into the model are the concentration of the chemical species of the reaction product in the gas circulatory system on the basis of earlier introducings and combustions of defined amounts of the aqueous medium.

In a further development of the invention, the introducing of further, defined amounts of sample and following ascertaining of concentration of the reaction product are repeated as long as the dynamic range of a measuring unit for determining the current value of the measured variable enables a sufficiently exact ascertaining of the concentration of the chemical species of the reaction product in the gas circulatory system, and only thereafter is the purging of the gas circulatory system with the carrier gas performed.

The method of the invention is especially suitable for monitoring total organic carbon (TOC) as water borne substance, wherein the reaction product is carbon dioxide, or total bound nitrogen (TNb), wherein the reaction product is nitrogen monoxide (NO).

The gas circulatory system is preferably a closed circulatory system during the reaction in the high temperature reaction chamber and the ascertaining of the current value of the measured variable.

The state modeling of the gas circulatory system enables, furthermore, a monitoring of the analytical system, with which the method is performed. For example, an alarm signal can be output, when the time change of the concentration of the chemical species of the reaction product in the gas circulatory system on the basis of contamination exceeds a limit value, since this can signal a diffusion leak above a critical size in the gas circulatory system.

In a further development, the time change of the concentration of the chemical species of the reaction product in the gas circulatory system on the basis of contamination is ascertained in time intervals, from which a rate of change of the time change of the concentration on the basis of contamination can be derived, wherein, additionally, an alarm signal is output, when, from the rate of change of the time change of the concentration on the basis of contamination and the current value of the time change of the concentration on the basis of contamination, the reaching of a limit value for the time change of the concentration on the basis of contamination is foreseeable in a predetermined time.

In a further development of the invention, a signal is generated, when, on the basis of the concentration of the chemical species of the reaction product in the gas circulatory system ascertained according to the model, another ascertaining of the concentration of the water borne substance in the aqueous medium is no longer possible with sufficient accuracy. Through the signal, for example, the above described purging step for cleaning the gas circulatory system can be introduced.

Condensation steps, for example, by means of a cold trap, or the filtering out of acids can, as needed, be implemented in the method.

BRIEF DESCRIPTION OF THE DRAWINGS

The invention will now be explained on the basis of an example of an embodiment, as illustrated in the drawing, the sole FIGURE of which shows as follows:

FIG. 1 a sketch of the principles of an analytical apparatus for TOC ascertainment with the method of the invention.

DETAILED DISCUSSION IN CONJUNCTION WITH THE DRAWINGS

The apparatus shown in FIG. 1 includes a gas circulatory system 1, in which a high temperature reaction chamber 2 is held at a temperature of 850° C. The gas circulatory system extends from there to a measuring chamber 3, which comprises an infrared photometer, in order to ascertain the $CO_2$ content in the gas circulatory system.

The gas circulatory system contains a carrier gas, for example, oxygen or filtered air containing only a negligible amount of $CO_2$. The carrier gas is, when required, allowed to flow from a reservoir 4 into the gas circulatory system via a first, controlled, metering valve, in order to purge the gas circulatory system, when the $CO_2$ content in the gas circulatory system becomes so high, that a measuring with sufficient accuracy is no longer possible. During the purging, a part the gas in the gas circulatory system is drained off at a controlled, outlet valve 6, in order, in this way, to dilute the $CO_2$ content in the gas circulatory system.

Further provided in the gas circulatory system are a condensing dryer 7 for removal of water and an acid filter 8 for removal of HCl and sulfuric acid.

For ascertaining TOC, a defined amount of aqueous medium can be metered in via a second, controlled, metering valve 5 either upstream of the high temperature reaction chamber 2 in the gas circulatory system 1 or directly into the high temperature reaction chamber.

The sample amount can be, for example, 100 µl up to about 1000 µl, for example, 400 to 600 µl, wherein the sample is metered in, for example, over a period of time of some tens of seconds up to 1 minute. The selected sample amount can depend, for example, on the expected TOC content and the sensitivity of the photometer.

The gas circulatory system is provided with a pump 9, in order to maintain a predetermined flow rate in the gas circulatory system. The flow rate is preferably so selected, that the cycle time for the gas volume is appropriate for the measurement task. Currently, it is preferred, that the cycle time be no longer than a minute and, further preferably, no longer than a half minute. In a currently preferred embodiment of the invention, the captured volume of the gas circulatory system amounts to about 600 ml, and the gas circulatory system has a flow rate of about 1.5 l/min.

The analytical apparatus 1 is controlled by a control and evaluation unit 10, which, on the one hand, ascertains contamination by $CO_2$ from the air in the surroundings on the basis of a diffusion model, and, on the other hand, registers and evaluates the measurement data of the photometer of the measuring chamber 3, in order to ascertain TOC on the basis of the ascertained, evolved $CO_2$. If, for example, a rise of the $CO_2$ content in the gas circulatory system from one sample to the next, as detected, was from 350 ppm to 390 ppm, while, on the basis of observation of the null signal of the photometer after the last purging with the carrier gas, a rate of contamination of 2 ppm/min was ascertained and the evaluation of a sample takes 2 min, then the $CO_2$ content in the gas circulatory system to be associated with the last sample is only 390 ppm−350 ppm−2×2 ppm=36 ppm. This value is used for TOC ascertainment.

The control and evaluation unit controls, furthermore, the purging of the gas circulatory system. An essential criterion for introducing a purging is the $CO_2$ content in the gas circulatory system. When, for example, the last measured value indicates, that the next measured value will exceed a limit value, then is a signal set, in order to perform the purging.

The invention claimed is:

1. A method for monitoring the concentration of a water borne substance in an aqueous medium, comprising the steps of:
   introducing a defined amount of the aqueous medium into a gas circulatory system of an analytical apparatus comprising a high temperature reaction chamber and a measuring chamber, wherein the gas circulatory system extends through the high temperature reaction chamber and the measuring chamber, and wherein the introducing of the aqueous medium occurs upstream of the high temperature reaction chamber or into it;
   evaporating the aqueous medium in the high temperature reaction chamber;
   reacting the water borne substance with at least one reaction partner in the high temperature reaction chamber to a gaseous reaction product;
   registering the current value of a measured variable, which is a function of the concentration of the chemical species of the reaction product in the gas circulatory system, wherein the concentration of the chemical species of the reaction product in the gas circulatory system depends, on the one hand, on a time-dependent state of the gas circulatory system and, on the other hand, on the concentration of the substance in the aqueous medium; and
   ascertaining the concentration of the substance in the aqueous medium by applying the current value of the measured variable, wherein:
   in the ascertaining of the concentration of the substance in the aqueous medium, the contribution to the concentration of the chemical species of the reaction product in the gas circulatory system by the state of the gas circulatory system is ascertained on the basis of a model of the state, and a correction of the concentration of the chemical species of the reaction product in the gas circulatory system occurs on the basis of this contribution;
   for producing a clean state of the gas circulatory system, the gas circulatory system is purged, at given times or state dependently, with a carrier gas, which is free of the chemical species of the reaction product, except for possible negligible impurities, and following purging with the carrier gas, a time behavior of the measured variable is observed without introducing additional sample of the aqueous medium, in order to win current data for modeling of time behavior of the contamination;
   the gas circulatory system is not purged with the carrier gas after each ascertaining of the concentration of the chemical species of the reaction product in the gas circulatory system, but, instead, there occurs, after a first introducing of a first defined amount of an aqueous medium into the gas circulatory system and following ascertaining of the concentration of the chemical species of the reaction product, at least one further introducing of a second defined amount of an aqueous medium into the gas circulatory system and, subsequently, the then present concentration of the chemical species of the reaction product is ascertained on the basis of the current value of the measured variable;
   the current concentration of the substance in the second defined amount of the aqueous medium is ascertained on the basis of the concentration of the chemical species of the reaction product in the gas circulatory system and the model of the state of the gas circulatory system, in which enter the concentration of the chemical species of the reaction product in the gas circulatory system as a result of earlier introducings and combustions of defined amounts of the aqueous medium.

2. The method as claimed in claim 1, further comprising the step of:
   registering the measured variable, directly after the purging with the carrier gas and before new introducing of the aqueous medium, as reference value, especially as a null point for describing a clean state of the gas circulatory system, for ascertaining concentration of the chemical species of the reaction product in the gas circulatory system.

3. The method as claimed in claim 1, wherein:
   the chemical species of the reaction product can get from the environment of the analytical apparatus as contaminant into the gas circulatory system; and the model describes time-dependent changing of the concentration of the chemical species of the reaction product in the gas circulatory system.

4. The method as claimed in claim 1, wherein:
   the modeling comprises a diffusion model describing the time dependent contamination by the chemical species of the reaction product getting into the gas circulatory system from the air in the surroundings of the analytical apparatus.

5. The method as claimed in claim 1, wherein:
   the substance comprises total organic carbon (TOC) and the reaction product is carbon dioxide, or the substance comprises total bound nitrogen (TNb), and the reaction product is nitrogen monoxide (NO).

6. The method as claimed in claim 1, wherein:
   the introducing of further, defined amounts of sample and following ascertaining of the concentration of the reaction product are repeated without purging the gas circulatory system with carrier gas as long as the dynamic range of a measuring unit for determining the current value of the measured variable enables a sufficiently exact ascertaining of the concentration of the chemical species of the reaction product in the gas circulatory system, and only thereafter is the purging of the gas circulatory system with the carrier gas performed.

7. The method as claimed in claim 1, wherein:
   the gas circulatory system, apart from the introducing of the aqueous medium during the combustion and ascertaining of the current value of the measured variable, is a closed circulatory system.

8. The method as claimed in claim 3, wherein:
an alarm signal is output, when change of the concentration of the chemical species of the reaction product in the gas circulatory system as a result of contamination with respect to time exceeds a limit value.

9. The method as claimed in claim 3, further comprising the step of:
generating a signal, when, on the basis of the concentration of the chemical species of the reaction product in the gas circulatory system ascertained according to the model, another ascertaining of the concentration of the water borne substance in the aqueous medium is no longer possible with sufficient accuracy.

10. The method as claimed in claim 9, wherein:
triggered by the signal, the gas circulatory system is purged, at given times or state dependently, with a carrier gas, which is free of the chemical species of the reaction product, except for possible negligible impurities.

11. A method for monitoring the concentration of a water borne substance in an aqueous medium, comprising the steps of:
introducing a defined amount of the aqueous medium into a gas circulatory system of an analytical apparatus comprising a high temperature reaction chamber and a measuring chamber, wherein the gas circulatory system extends through the high temperature reaction chamber and the measuring chamber, and wherein the introducing of the aqueous medium occurs upstream of the high temperature reaction chamber or into it;
evaporating the aqueous medium in the high temperature reaction chamber;
reacting the water borne substance with at least one reaction partner in the high temperature reaction chamber to a gaseous reaction product;
registering the current value of a measured variable, which is a function of the concentration of the chemical species of the reaction product in the gas circulatory system, wherein the concentration of the chemical species of the reaction product in the gas circulatory system depends, on the one hand, on a time-dependent state of the gas circulatory system and, on the other hand, on the concentration of the substance in the aqueous medium; and
ascertaining the concentration of the substance in the aqueous medium by applying the current value of the measured variable, wherein:
in the ascertaining of the concentration of the substance in the aqueous medium, the contribution to the concentration of the chemical species of the reaction product in the gas circulatory system by the state of the gas circulatory system is ascertained on the basis of a model of the state, and a correction of the concentration of the chemical species of the reaction product in the gas circulatory system occurs on the basis of this contribution;
for producing a clean state of the gas circulatory system, the gas circulatory system is purged, at given times or state dependently, with a carrier gas, which is free of the chemical species of the reaction product, except for possible negligible impurities and which is allowed to flow from a reservoir into the gas circulatory system;
directly after the purging, registering the measured variable with the carrier gas and before new introducing of the aqueous medium, as a reference value, especially as a null point for describing a clean state of the gas circulatory system, for ascertaining the concentration of the chemical species of the reaction product in the gas circulatory system; and
observing the time dependent behavior of the measured variable without introducing additional sample of the aqueous medium, following purging with the carrier gas, in order to win current data for modeling of the time dependent behavior of the contamination;
wherein the modeling comprises a diffusion model describing the time dependent contamination by the chemical species of the reaction product getting into the gas circulatory system from the air in the surroundings of the analytical apparatus; and
wherein the chemical species of the reaction product can get from the environment of the analytical apparatus as contaminant into the gas circulatory system, and the model describes time-dependent changing of the concentration of the chemical species of the reaction product in the gas circulatory system.

12. The method as claimed in claim 11, wherein:
the substance comprises total organic carbon (TOC) and the reaction product is carbon dioxide.

13. A method for monitoring the concentration of a water borne substance in an aqueous medium, comprising the steps of:
introducing a defined amount of the aqueous medium into a gas circulatory system of an analytical apparatus comprising a high temperature reaction chamber and a measuring chamber, wherein the gas circulatory system extends through the high temperature reaction chamber and the measuring chamber, and wherein the introducing of the aqueous medium occurs upstream of the high temperature reaction chamber or into it;
evaporating the aqueous medium in the high temperature reaction chamber;
reacting the water borne substance with at least one reaction partner in the high temperature reaction chamber to a gaseous reaction product;
registering the current value of a measured variable, which is a function of the concentration of the chemical species of the reaction product in the gas circulatory system, wherein the concentration of the chemical species of the reaction product in the gas circulatory system depends, on the one hand, on a time-dependent state of the gas circulatory system and, on the other hand, on the concentration of the substance in the aqueous medium; and
ascertaining the concentration of the substance in the aqueous medium by applying the current value of the measured variable, wherein:
in the ascertaining of the concentration of the substance in the aqueous medium, the contribution to the concentration of the chemical species of the reaction product in the gas circulatory system by the state of the gas circulatory system is ascertained on the basis of a model of the state, and a correction of the concentration of the chemical species of the reaction product in the gas circulatory system occurs on the basis of this contribution;
the chemical species of the reaction product can get from the environment of the analytical apparatus as contaminant into the gas circulatory system; and
the model describes time-dependent changing of the concentration of the chemical species of the reaction product in the gas circulatory system due to contamination;
wherein an alarm signal is output, when change of the concentration of the chemical species of the reaction product in the gas circulatory system on the basis of contamination with respect to time exceeds a limit value.

14. The method as claimed in claim 13, wherein:
the modeling comprises a diffusion model describing the time dependent contamination by the chemical species of the reaction product getting into the gas circulatory system from the air in the surroundings of the analytical apparatus.

15. The method as claimed in claim 14, wherein:
for producing a clean state of the gas circulatory system, the gas circulatory system is purged, at given times or state dependently, with a carrier gas, which is free of the chemical species of the reaction product, except for possible negligible impurities.

16. The method as claimed in claim 15, further comprising the step of:
registering the measured variable, directly after the purging with the carrier gas and before new introducing of the aqueous medium, as reference value, especially as a null point for describing a clean state of the gas circulatory system, for ascertaining the concentration of the chemical species of the reaction product in the gas circulatory system.

17. The method as claimed in claim 16, further comprising the step of:
observing the time-dependent behavior of the measured variable without introducing additional sample of the aqueous medium, following purging with the carrier gas, in order to win current data for modeling of time-dependent behavior of the contamination.

18. The method as claimed in claim 14, wherein:
the substance comprises total organic carbon (TOC) and the reaction product is carbon dioxide, or the substance comprises total bound nitrogen (TNb), and the reaction product is nitrogen monoxide (NO).

* * * * *